United States Patent [19]

Moore

[11] Patent Number: 4,635,111

[45] Date of Patent: Jan. 6, 1987

[54] OPTICAL FIBER INSPECTION SYSTEM

[75] Inventor: Francis W. Moore, Richland, Wash.

[73] Assignee: The United States of America as represented by the United States Department of Energy, Washington, D.C.

[21] Appl. No.: 720,448

[22] Filed: Apr. 5, 1985

[51] Int. Cl.$^4$ .............................................. H04N 7/18
[52] U.S. Cl. ..................................... 358/106; 358/93; 358/97; 358/100; 358/901; 209/655; 209/587
[58] Field of Search ................... 358/93, 97, 100, 106, 358/101, 108, 901; 250/223 R; 356/237, 426; 364/501; 376/101; 209/539, 576, 577, 655, 587, 209/564, 910, 657, 581

[56] References Cited

U.S. PATENT DOCUMENTS

| | | | |
|---|---|---|---|
| 2,272,842 | 2/1942 | Hickok . | |
| 2,726,762 | 12/1955 | Aubry | 209/657 |
| 3,761,612 | 9/1973 | Alpers . | |
| 3,765,533 | 10/1973 | Stephens et al. | 358/106 |
| 3,821,732 | 6/1974 | Romney | 340/380 |
| 3,872,238 | 3/1975 | Herndon | 178/6 |
| 4,082,188 | 4/1978 | Grimmell et al. | 209/73 |
| 4,190,318 | 2/1980 | Upton, Jr. | 350/96.2 |
| 4,194,634 | 3/1980 | Kelly | 209/576 |
| 4,198,654 | 4/1980 | Coulomb | 358/109 |
| 4,203,673 | 5/1980 | Buckson | 209/587 |
| 4,259,948 | 4/1981 | Urban | 128/6 |
| 4,358,202 | 11/1982 | Puffer et al. | 356/430 |
| 4,377,238 | 3/1983 | Wilks et al. | 209/587 |
| 4,454,029 | 6/1984 | Codding | 209/581 |
| 4,568,972 | 2/1986 | Arents | 358/108 |

Primary Examiner—James J. Groody
Assistant Examiner—John K. Peng
Attorney, Agent, or Firm—Edward W. Nypaver; Robert Southworth, III; Judson R. Hightower

[57] ABSTRACT

A remote optical inspection system including an inspection head. The inspection head has a passageway through which pellets or other objects are passed. A window is provided along the passageway through which light is beamed against the objects being inspected. A plurality of lens assemblies are arranged about the window so that reflected light can be gathered and transferred to a plurality of coherent optical fiber light guides. The light guides transfer the light images to a television or other image transducer which converts the optical images into a representative electronic signal. The electronic signal can then be displayed on a signal viewer such as a television monitor for inspection by a person. A staging means can be used to support the objects for viewing through the window. Routing means can be used to direct inspected objects into appropriate exit passages for accepted or rejected objects. The inspected objects are advantageously fed in a singular manner to the staging means and routing means. The inspection system is advantageously used in an enclosure when toxic or hazardous materials are being inspected.

1 Claim, 10 Drawing Figures

OPTICAL FIBER INSPECTION SYSTEM

TECHNICAL FIELD

The technical field of this invention is inspection apparatus and systems for optical inspection of nuclear fuel pellets and other objects for which optical inspection of exterior surfaces is required. The U.S. government has rights in this invention pursuant to contract No. DE-AC14-76FF02170 between the U.S. Department of Energy and Westinghouse Hanford Company.

BACKGROUND OF THE INVENTION

Current practice in the nuclear industry requires fabrication of relatively small (10 millimeter diameter) cylindrical nuclear fuel pellets. These nuclear fuel pellets are typically assembled end-to-end within an elongated cylindrical tube, often termed cladding. The strict requirements for safety and quality in the nuclear industry requires the cylindrical surface of fuel pellets to be optically inspected prior to assembly into the cladding to make fuel pins. Optical inspection is needed to assure that the cylindrical surfaces are not irregular, pitted, or otherwise defective since such defects can cause localized overheating which may damage or cause failure of the fuel pin cladding.

Nuclear fuels are typically radioactive and can also be chemically toxic to human beings. Toxicity is a particular problem with plutonium fuels and fuels containing mixed oxides of plutonium and uranium. Such toxic or radioactive pellets cannot be handled by humans and therefore must be remotely inspected.

The prior art includes U.S. Pat. No. 4,377,238 to Wilks et al. The Wilks patent discloses a method and apparatus using optics for inspecting nuclear fuel pellets for surface defects. The Wilks apparatus utilizes a laser beam which is scanned across the surface of a rotating pellet using a rotating polygonal mirror. Light images reflected from the surface of the rotating fuel pellet are detected by a photocell. Image signals for small individual image points are compiled on computer and analyzed to produce a quality index used to discriminate acceptable from not acceptable fuel pellets. Operational difficulties were experienced with inventions constructed according to the Wilks et al patent because of the complexity and small tolerance for error associated with rapidly scanning a laser beam across a rapidly revolving fuel pellet.

The prior art also includes U.S. Pat. No. 4,082,188 to Grimmel et al, entitled Apparatus For Color Recognition And Defect Detection Of Objects Such As Capsules. The Grimmel patent discloses a system for automatically inspecting, analyzing and eliminating defective pharmaceutical capsules based on the optical characteristics of the exterior surfaces of the capsules. Focused light is reflected off of the capsules and gathered by two lens subsystems specially adapted for color recognition and structural defect recognition. Both subsystems employ photodetectors such as photomultipliers to transform the optical beams into analog electronic signals. The analog signals are converted into digital signals and a computer is used to compile and analyze the information. Instructions can then be made to reject defective capsules.

SUMMARY OF THE INVENTION

It is an object of this invention to provide an inspection system for optically inspecting exterior surfaces of nuclear fuel pellets or other objects from a remote position.

It is another object of the invention to provide a system for accurately and reliably inspecting nuclear fuel pellets or other objects to determine surface contamination in the form of stains and discolorations, irregularities in surface contour, and mechanical defects which may be deleterious to the heat transfer and mechanical properties of such objects.

It is a further object of the invention to provide an apparatus for remotely inspecting nuclear fuel pellets or other objects which does not require rotation of the objects in order to inspect the lateral peripheral surfaces of the objects.

Additional objects, advantages and novel features of the invention will be set forth in part in the description which follows, and in part will become apparent to those skilled in the art upon examination of the following or may be learned by practive of the invention. The objects and advantages of the invention may be realized and attained by means of the instrumentalities and combinations particularly pointed out in the appended claims.

To achieve the foregoing and other objects and in accordance with the purposes of the present invention, as embodied and broadly described herein, inspection systems according to this invention may comprise an inspection head having a pellet receiving passageway extending thereinto. A transparent tubular window is provided at an advantageous point along the passageway through which light can be beamed and reflected back to a plurality of lenses. The plurality of lenses are preferably mounted at spaced circumferential positions about the window to allow full viewing of lateral peripheral surfaces of the objects being inspected.

Coherent optical fiber light guides receive images transmitted through the lenses and convey them onwardly to an image transducer. The image transducer, such as a television camera, transforms the optical images into electronic signals. The electronic signals can easily be transmitted, stored, processed and/or displayed upon an image viewer such as a television monitor. Signal processing using a computer or other means can advantageously be used to provide an integrated image of the peripheral surfaces of the object being inspected.

Inspection systems of this invention are advantageously used in conjunction with an airtight or other enclosure when toxic or hazardous materials are being inspected. Objects being inspected within the enclosure can be fed to the inspection head by an infeed mechanism which can also advantageously orient the objects end-to-end for passage into the inspection head.

The inspection systems also advantageously include a staging means for supporting objects adjacent to the window and then releasing the objects after being inspected. Means for controllably diverting inspected objects into accepted, rejected or other exit passageways are also preferably included.

Preferred forms of the invention described herein beneficially allow remote simultaneous inspection of the full lateral peripheral surfaces of the objects. Rotation of the objects to gain full peripheral viewing is obviated thereby reducing the mechanical and operational complexity of the systems when compared to the prior art. Use of coherent optical fiber light guides allows the object images to be conveyed to image transducers mounted outside the enclosure for ease of maintenance and better operating conditions. Transformation of the image into electronic signals allows greater signal processing and enhancement capability plus improved convenience and greater flexibility for the operator. Other advantages and benefits of the invention will be apparent from the description given herein or from practice of the invention.

BRIEF DESCRIPTION OF THE DRAWINGS

The accompanying drawings which are incorporated in and form a part of this specification illustrate a preferred embodiment of the invention and when combined together with the description, serve to explain the principles of the invention. In the drawings.

DETAILED DESCRIPTION OF THE PREFERRED EMBODIMENT

Reference will now be made in detail to the present preferred embodiment of the invention, an example of which is illustrated in the accompanying drawings.

Figure 1:
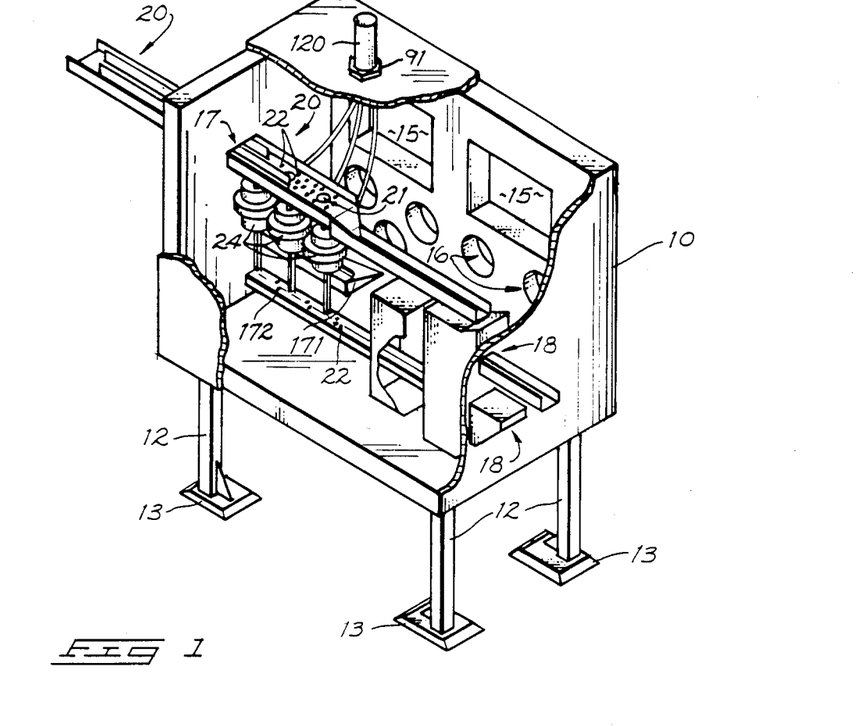
FIG. 1 is a perspective view of portions of an inspection system mounted within an enclosure, portions of the enclosure and system have been removed to show the relative positions of various components.

FIG. 1 shows an airtight enclosure 10. Enclosure 10 is not a necessary requisite to practice of the invention, it is, however, commonly used with the invention when direct inspection is not possible due to toxicity, radiation or other hazards to direct human handling. There may be situations where application requirements would not necessitate such an enclosure even though the remote inspection system of this invention is preferred and operable.

Enclosure 10 advantageously includes a supporting structural framework 12 which can be secured to foundation 13 or other appropriate support. Enclosure 10 is advantageously provided with viewing windows 15, and gloved access ports 16. Infeed port 17 and outfeed ports 18 are also included so that the nuclear fuel pellets or other objects being inspected can be conveyed into and from enclosure 10, respectively.

FIG. 1 also shows an infeed means such as a vibratory infeed conveyor 20. Infeed conveyor 20 conveys pellets 22 to points superjacent to three inspection heads 24. Fuel pellets 22 drop from conveyor 20 through apertures 21 and into collimator means 26 (see FIG. 2) associated with each inspection head 24.

Figure 2:
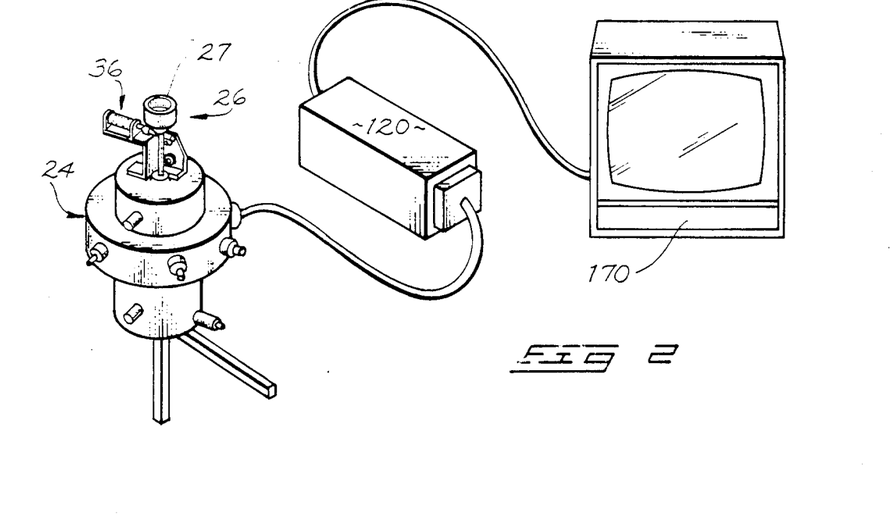
FIG. 2 is a schematic drawing showing the basic relationship between an inspection head, optical fiber light guides transmitting light images from the inspection head to a television camera or other image transducer, and a television monitor or other image viewing means connected thereto for remotely displaying representative images of objects being inspected.

Collimators 26 receive fuel pellets 22 in entry funnels 27. The interior surfaces of funnels 27 are shaped so that cylindrical pellets 22 are collimated to stand with adjacent end surfaces flat against one another rather than entering the inspection head in random orientations. The collimating action of collimator 26 is also accomplished by vibrating funnels 27 with mechanical vibrators 36.

Figure 3:
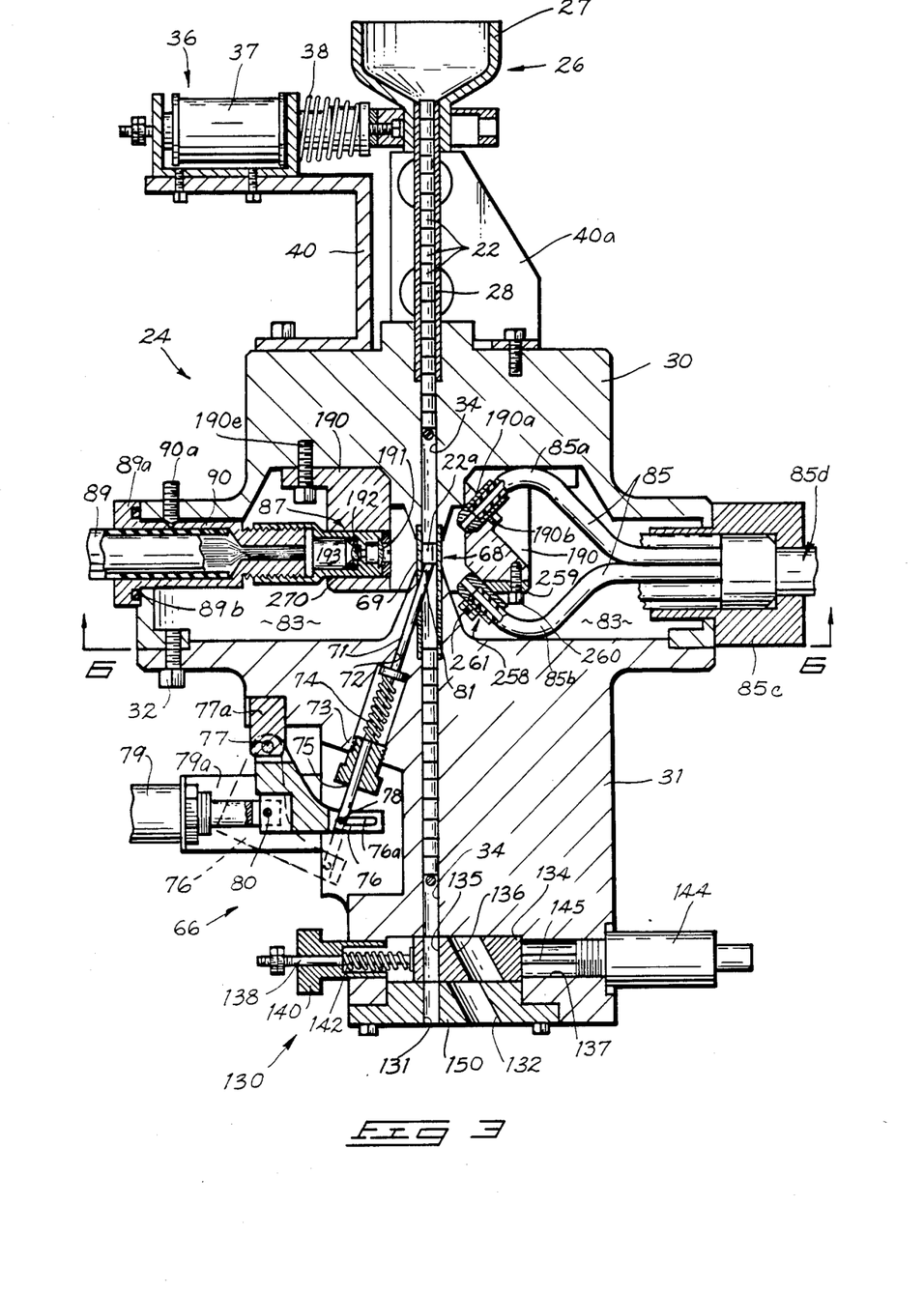
FIG. 3 is an enlarged sectional view of one inspection head assembly as shown in FIG. 1 taken along line 3—3 of FIG. 5.

FIG. 3 shows mechanical vibrators 36 include electrically powered oscillating coils 37 with return springs 38. Vibrators 36 are mechanically coupled to the base of entry funnels 27 so as to transfer vibrations thereto. Support brackets 40 and 40a are connected to inspection heads 24 for mounting mechanical vibrators 36 and the inflow sensor system described below. Mechanical vibrators 36 vibrate the entry funnel 27 and funnel stem 28 thereby causing incoming cylindrical fuel pellets 22 to be fed into the funnel stem 28 in an end-to-end orientation.

FIGS. 3-6 show a preferred embodiment inspection head 24 constructed according to this invention. Inspection head 24 includes an upper head piece 30 and a lower head piece 31. Upper and lower head pieces 30 and 31 are connected together by a plurality of fasteners or other connection means 32.

Centrally located within inspection head 24 is an object passageway 34. Object passageway 34 is preferably linear and approximately vertically oriented along the longitudinal axis of inspection head 24, although other configurations are possible. Entry funnel 27 and funnel stem 28 of collimating means 26 are aligned and communicate with object passageway 34 so that fuel pellets 22 drop downwardly from funnel stem 28 into object passageway 34. The inflow of fuel pellets 22 through funnel stems 28 is continuously monitored by an inflow sensor system 42.

Figure 4:
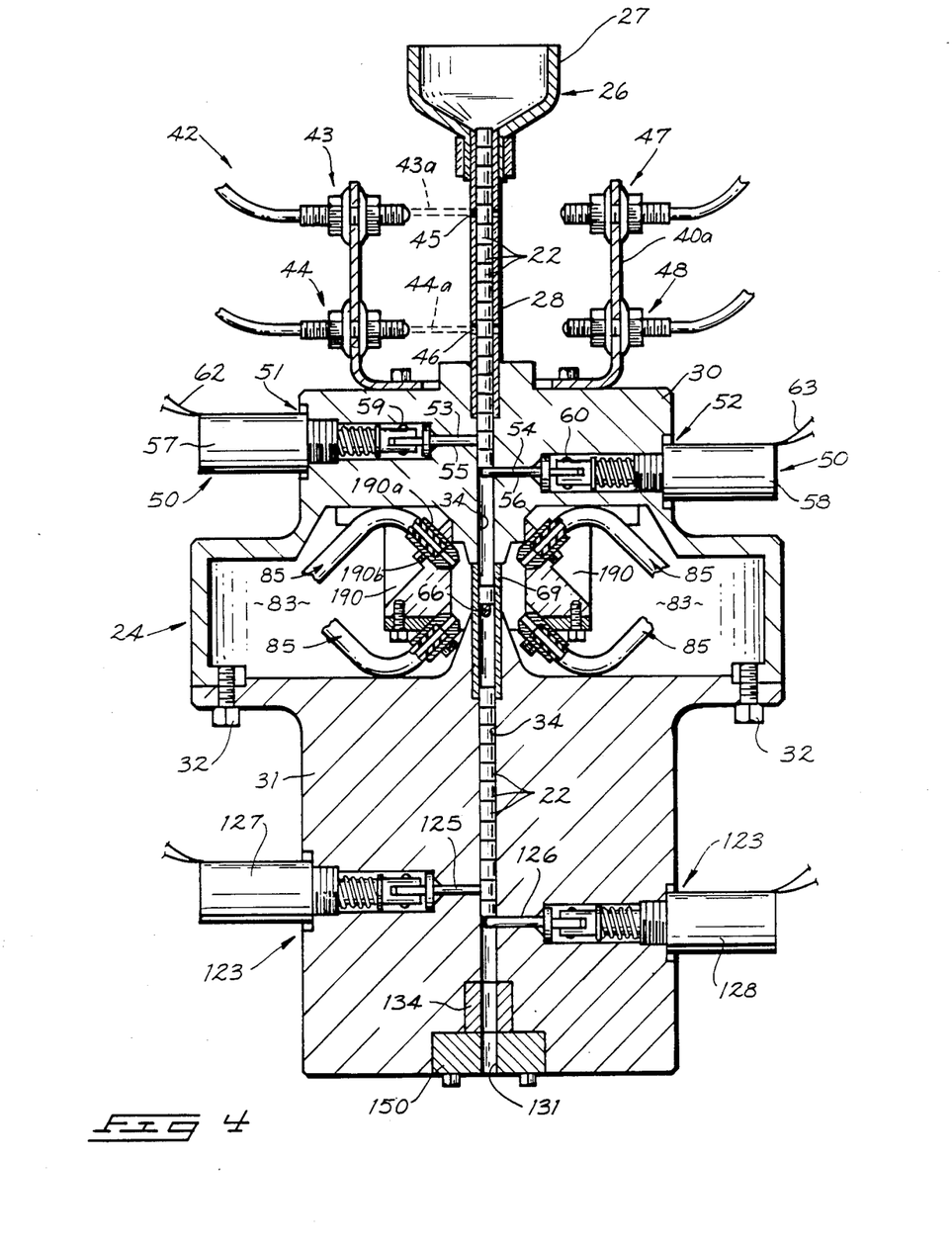
FIG. 4 is a sectional view of the inspection head assembly of FIG. 3 taken along line 4—4 of FIG. 5; the mechanical vibrator 36 shown in FIGS. 3 and 5 has been omitted for greater clarity.
Figure 5:
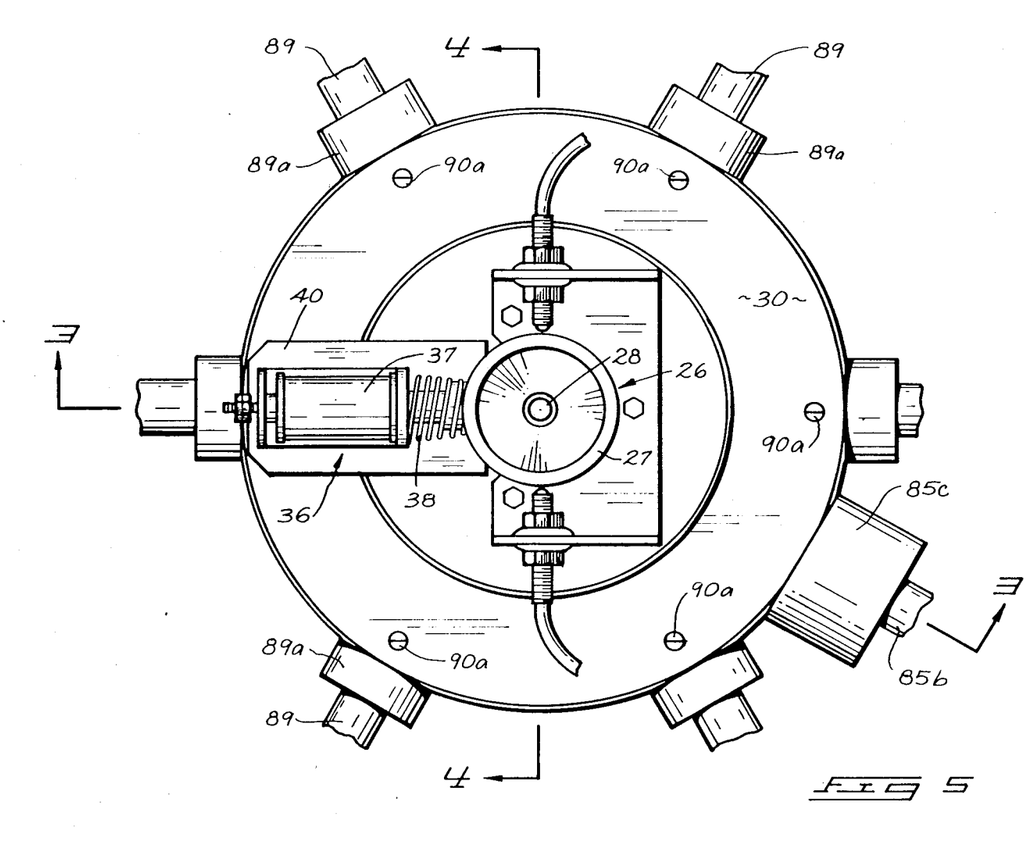
FIG. 5 is a top view of the inspection head assembly shown in FIG. 3.

FIG. 4 shows a preferred inflow sensor system which advantageously includes an upper lamp or other beam producing means 43 and a lower lamp or other beam producing means 44. Light, infrared or other wavelength beams 43a and 44a are respectively produced by upper and lower beam producing means 43 and 44. Beams 43a and 44a are directed through upper and lower transverse apertures 45 and 46, respectively, formed through the walls of funnel stem 28. When pellets 22 are not present, beams 43a and 44a strike photosensors 47 and 48. The resulting signals are used to warn the operator that fuel pellets are not passing through funnel stem 28.

The inspection head upper head piece 30 is preferably equipped to feed pellets 22 singularly into position for inspection. FIG. 4 shows an upper singular feed 50 which comprises first and second slide pin assemblies 51 and 52. First and second slide pin assemblies 51 and 52 include first and second slide pins 53 and 54 which are slidably mounted within apertures 55 and 56. First and second slide pins 53 and 54 are mechanically connected to linear motion solenoid units 57 and 58 using pins 59 and 60 or other connection means well known in the art. Electrical energy is supplied through first and second wire sets 62 and 63 to solenoids 57 and 58, respectively, to provide electrical control for singularly feeding incoming pellets 22.

A window means 68 such as window 69 is provided along object passageway 34 at a location below upper singular feed 50 so that optical inspection of the entire lateral or side peripheral surfaces of the pellet or other object can be performed. The window is preferably a cylindrical, transparent tubular conduit 69 mounted between upper and lower head pieces 30 and 31. Tubular window 69 is preferably constructed of clear quartz thereby allowing 360 degree transparency for both light transmission into passageway 34 and observation of light reflected from the pellets back through the tubular window.

A staged pellet 22a being inspected within window 69 is supported upon a staging mechanism 66 shown most clearly in FIG. 3.

FIG. 3 shows a preferred construction of staging mechanism 66. Staging mechanism 66 preferably comprises a staging pin 71 which is slidably positioned within a staging aperture 72. A ferrule 73 is threadably received in lower head piece 31 near the outer end of staging aperture 72. Staging pin 71 extends through a spring 74 or other biasing means and through a central aperture 75 in ferrule 73. Staging pin 71 is connected to a pivot arm 76 by pivot pin 78 which is pivotable and slidable within slot 76a. Pivot arm 76 is pivotally connected to lower head piece 31 at pivot 77 using bracket 77a.

A linear motion solenoid 79 is povitally connected to pivot arm 76 at pivot 80. Solenoid 79 is mounted to lower head piece 31 using bracket 79a. Linear motion by solenoid 79 causes pivot arm 76 to pivot between the extended position shown in solid lines in FIG. 3 and the retracted position shown in phantom. The attached staging pin 71 also moves between extended and retracted positions. In the extended position the contact end 81 of staging pin 71 extends within passageway 34 and supports a staged pellet 22a within window 69. In the retracted position staging pin 71 is retracted from passageway 34 so that staged pellet 22a can drop freely therethrough.

Inspection head 24 is constructed with an optical chamber 83 in which optical inspection equipment is installed. Optical chamber 83 is advantageously formed between the bottom of upper head piece 30 and the top of lower head piece 31. Optical chamber 83 is an annularly shaped chamber about the periphery of window means 68.

Mounted within optical chamber 83 are a plurality of light source guides 85 for transmitting light to illuminate the exterior of staged pellet 22a. Light guides 85 are preferably arranged at spaced angular positions about the periphery of window means 69 thereby allowing the pellet exterior surfaces to be fully illuminated (see FIG. 6).

It is advantageous to provide light guides 85 which are directed from both above and below for good illumination of the lateral peripheral surfaces of staged pellet 22a. FIG. 4 shows an upper row 85a of light guides which shine downwardly at approximately a 45 degree angle to the longitudinal axes of passageway 34 and pellet 22a contained therein. FIG. 4 also shows a lower row 85b which shines from below upwardly at approximately a 45 degree angle to such longitudinal axes.

Light guides 85 are mounted within chamber 83 using a locating ring 190. Locating ring 190 is mounted to the bottom of upper head piece 31 using fasteners 190e. Upper light source guides 85a extend through apertures 190a formed in locating ring 190 and are secured therein by set screws 190b. Lower light source guides 85b extend through apertures 258 formed in a mounting piece 259 which is fastened to locating ring 190 by fastener 260. Set screws 261 secure the light source guides 85b in apertures 258.

FIG. 3 shows light source guides 85 advantageously assembled into a cable 85d which is supported by a light guide fitting 85c where the cable enters inspection head 24. Light guide cable 85d extends from fitting 85c to a light source penetration fitting 93 shown in FIGS. 9 and 10, which is mounted in a wall of enclosure 10. A light source (not shown) is mounted outside of enclosure 10 for ease of maintenance. Exterior mounting of the light source requires airtight penetration of light beams into the enclosure for subsequent conveyance along light guides 85. Penetration fitting 93 allows light from the light source to enter enclosure 10 while maintaining airtight construction.

Figure 9:
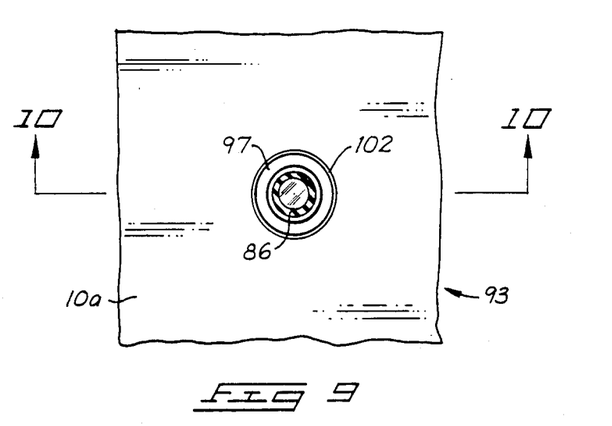
FIG. 9 is an enlarged side elevational view of a light penetration used to conduct light across the enclosure wall for illuminating objects being inspected within the inspection head.
Figure 10:
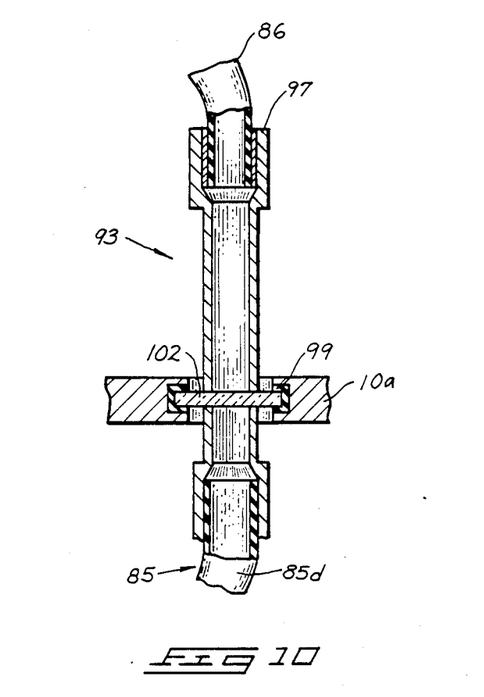
FIG. 10 is a cross-sectional view taken along line 10—10 of FIG. 9.

Penetration fitting 93 is shown in enlarged detail in FIGS. 9 and 10. Light from the external light source is conveyed through an incoming light guide 86 provided with an end fitting 97 adapted to abut against a window 102 secured in a fluid tight relation within enclosure wall 10a by means of a gasket 99. Light conveyed by guide 86 is beamed across window 102 and into light guide 85 which is adapted to abut window 102.

Light transferred through light guide 86, penetration fitting 93 and light guide 85 is beamed through tubular window 69 and onto the surfaces of staged pellet 22a. Light rays reflect off of the surfaces of the staged pellet or other object and are collected by a plurality of lens assemblies 87 (see FIGS. 3 and 6) which are positioned at spaced angular positions about tubular window 69.

Figure 6:
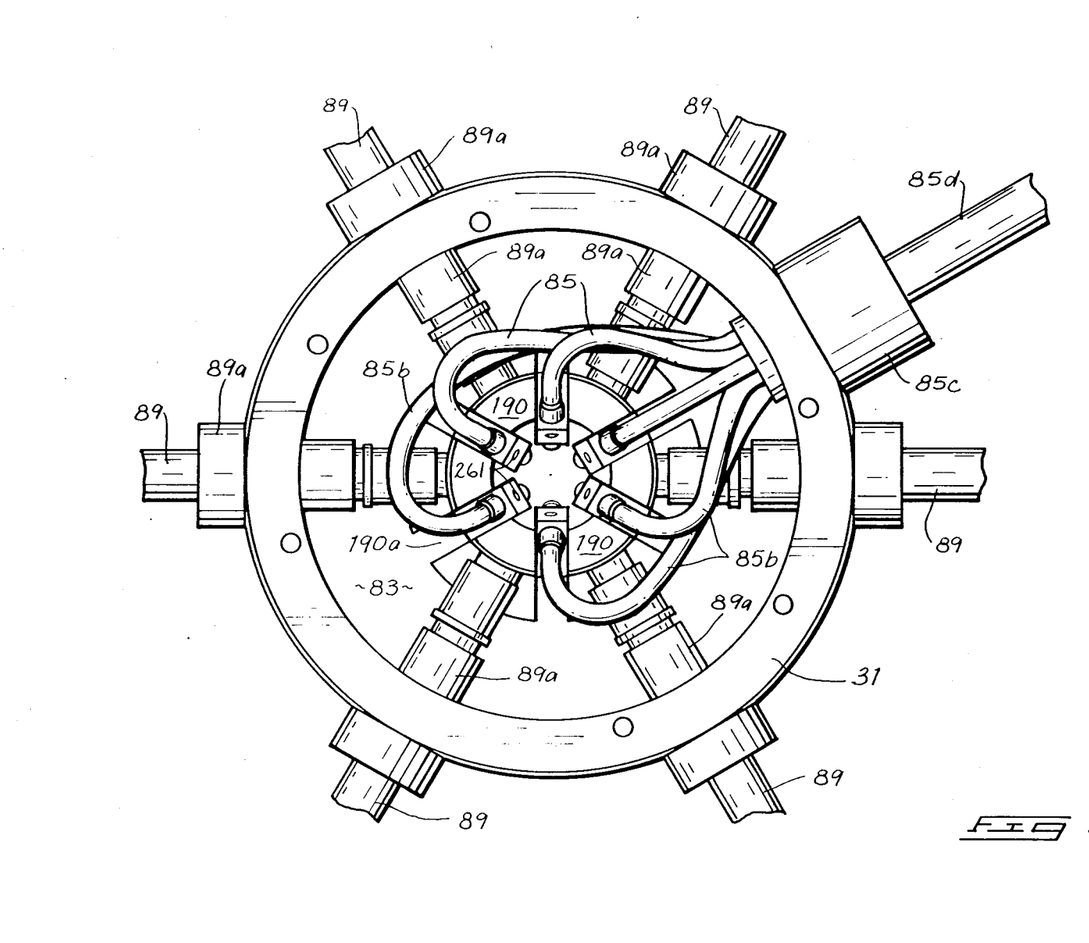
FIG. 6 is an auxillary bottom view of the inspection head of FIG. 3 with the lower head piece 31 removed; taken along line 6—6 of FIG. 3.

In the preferred embodiment there are six lens assemblies 87 positioned at approximately 60 degree spacings about the window. Lens assemblies 87 are mounted to upper head piece 30 using locating ring 190 which is provided with apertures 270 for receiving the lens assemblies therein.

Lens assemblies 87 can include an objective lens 191 and a concave convex lens 192 mounted within a lens barrel 193. Portions of lens barrel 193 can be provided with interior threads (not shown) for mounting lenses 191 and 192 therein.

Lens assemblies 87 are each capable of gathering light from over a field of view which overlaps with adjacent lens assemblies. Overlap of the viewing field of adjacent lens assemblies allows for a complete viewing of the lateral peripheral surfaces of pellets 22.

Lens assemblies 87 are each optically coupled to coherent optical fiber light guides 89. Optical fiber light guides 89 are constructed of a plurality of very small optical fibers. The optical fibers used to construct the light guides 89 are manufactured so that the optical fibers produce a coherent optical image accurately representing the image gathered by lens assemblies 87.

FIGS. 3 and 6 show that light guides 89 exit from the inspection head 24 through light guide apertures 90. Light guide apertures 90 are provided with set screws 90a which engage and hold the light guide end fitting assembly 89a in position within inspection head 24. Light guide end fitting assembly 89a is advantageously provided with an O ring or other seal 89b to exclude dust from the optical components.

Figure 7:
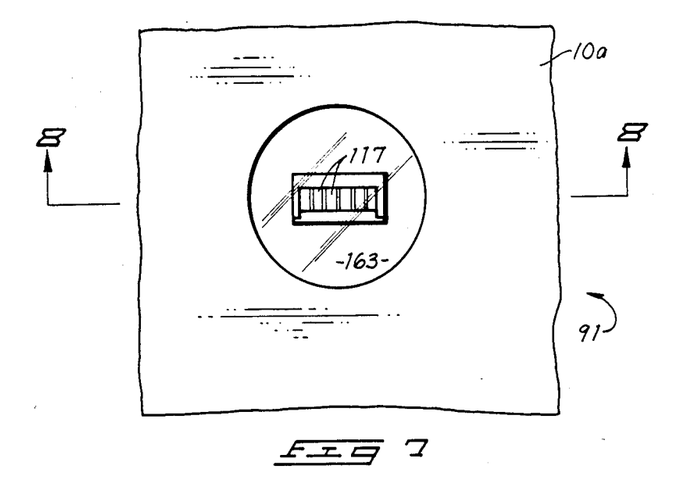
FIG. 7 is an enlarged side elevational view of a light penetration used to conduct the light images across the enclosure wall.
Figure 8:
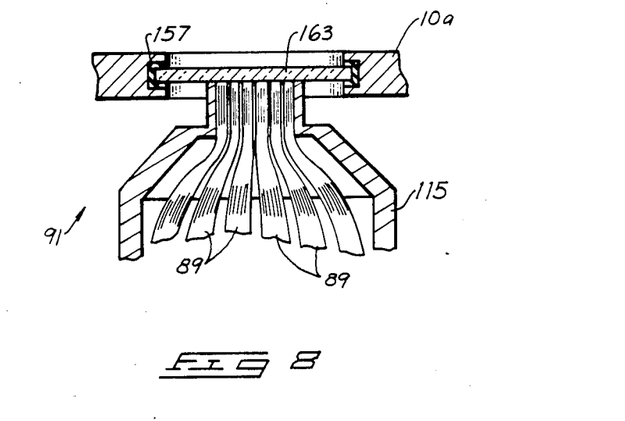
FIG. 8 is a cross-sectional view taken along line 8—8 of FIG. 7.

Light guides 89 extend from inspection head 24 to a penetration fitting 91 shown in detail in FIGS. 7 and 8. Penetration fitting 91 allows the optical images from each lens assembly 87 and light guide 89 to be conveyed from the interior of enclosure 10 to the exterior thereof while maintaining an airtight seal.

FIGS. 7 and 8 show one form of a suitable penetration fitting 91 used in conjunction with a closed circuit television camera 120 mounted outside of airtight enclosure 10. Penetration fitting 91 includes a transparent bottom end piece or window 163 secured in a fluid tight relation within enclosure wall 10a by means of a gasket 157. A camera objective lens is positioned against the window 163 so that the image conveyed therethrough can be perceived and converted into an electronic television signal.

Coherent optical fiber bundles forming light guides 89 are arranged together by end piece 115 to provide, in this case, six individual approximately rectangular images 117 adjacent to window 163. These six individual images are perceived by the television camera 120 and the resulting signal can be displayed directly on a monitor 170 (FIG. 2) or processed further as discussed below.

Pellets 22 inspected by the optical system just described are discharged downwardly by retracting staging pin 71. Discharged pellets drop along passageway 34 into a holding position within lower headpiece 31. FIG. 4 shows a plurality of pellets 22 so held by a second or lower means for singularly feeding pellets 123. Lower singular feed 123 is constructed similarly to the upper singular feed 50. Lower singular feed 123 comprises third and fourth slide pin assemblies 125 and 126. Third and fourth slide pin assemblies 125 and 126 are preferably provided with linear motion solenoids 127 and 128, respectively, thereby allowing electronic control of pellet discharge from passageway 34.

FIG. 3 shows that lower head piece 31 includes a routing mechanism 130 for directing inspected pellets into either a first exit passageway 131 or a second exit passageway 132. First exit passageway 131 is preferably for receiving acceptable pellets. Second exit passageway 132 is preferably for receiving rejected pellets. Both exit passageways 131 and 132 are formed in support piece 150 which is mounted to the bottom of lower head piece 31 and which holds a slidable routing block 134 in position.

Routing block 134 has a first passageway 135 and a second passageway 136. Routing block 134 is slidable within cavity 137 formed in lower head piece 31. Routing mechanism 130 also includes routing block slide pin 138 which extends outwardly and through a guide piece 140. A biasing compression spring 142 is provided between guide piece 140 and routing block 134. Routing block 134 is also connected to a linear motion solenoid 144 via connection pin 145.

Solenoid 144 moves routing block 134 between first and second positions within cavity 137. In the first position shown in FIG. 3 the first passageway 135 is aligned with passageway 34 thereby allowing the discharging pellets to flow therethrough and on through exit passageway 131. Accepted pellets drop onto an accepted pellet outfeed 172 (FIG. 1) by which they are conveyed from enclosure 10 to other pellet handling equipment. In the second position the routing block 134 is offset to the left (not shown) thereby positioning second exit passageway 136 beneath passageway 34 and aligned with rejected pellet exit passageway 132. Rejected pellets exit through the rejected pellet exit passageway 132 and into a rejected pellet container 171 (FIG. 1) or conveyor (not shown) for subsequent handling.

Inspection systems according to this invention can advantageously include signal processing equipment (not shown) between the television camera 120 and monitor 170 (FIG. 2). Signal processing equipment is known in the art of television signal processing equipment and computer generated television signals. A variety of signal processing systems can be used. It is preferred that a signal processing system be provided which allows the plurality of discrete images originating from the individual lens assemblies 87 to be integrated to provide a single display of the pellet side surfaces. Such integrated display could be presented in a rectangular image on monitor 170. This real image can be processed by human visual inspection or by image processing equipment for automated inspection.

The manner of using the invention will now be described more fully. A plurality of pellets 22 or other objects are fed into enclosure 10 through an infeed port 17 using vibratory conveyor 20. Adjacent handling equipment may be mounted directly to enclosure 10 to maintain an airtight seal if necessary or desired. The infed pellets fall from infeed conveyor 20 through apertures 21 into the vibrating collimating funnel 27 and pass through funnel stem 28. The incoming pellets are inventoried by upper singular feed 50.

Upper singular feed 50 provides singular feeding of pellets 22 by first extending the second or lower slide pin 54 through aperture 55 and into object passageway 34. Any pellets 22 falling downwardly are stopped by slide pin 54 when so extended. First slide pin 53 is spaced one pellet higher along passageway 34. When there are two or more pellets supported upon slide pin 54, then first slide pin 53 can be extended to force the second pellet against the side walls of passageway 34 thereby holding it in position. Second slide pin assembly 52 can then be controlled so that slide pin 54 is withdrawn from beneath the bottom pellet 22. This allows only the bottom pellet to fall downwardly and into position upon staging mechanism 66 for inspection.

Light from source light guides 85 is beamed through tubular window 69 and onto the exterior surfaces of staged pellet 22a. Light reflected from the side or lateral peripheral surfaces of pellet 22a is gathered by lens assemblies 87 and conveyed onwardly through coherent optical fiber light guides 89. The light images conveyed by light guides 89 are passed through window 163 and perceived by a closed circuit television camera 120 or other image transducer which converts the light images into electronic signals representative of the optical images.

Electronic signals from television camera 120 are electronically sent to a high resolution television monitor 170 or other signal viewing means. It is desirable to have a signal processing system (not shown) between television camera 120 and monitor 170. The signal processing system advantageously converts the electronic signal into digital form, if not already in such form. After the signal is digitized, it can be processed by a suitable computer so that the individual peripheral segments of the pellet can be integrated into a singular image depicting the total circumference of the cylindrical pellet sides. Such an image processing system is advantageous for providing an easy to interpret single image displaying the peripheral surfaces of the object being inspected. Such signal processing is not necessary for practicing the invention described herein.

It is also desirable to include an image processing system so that the images obtained by the inspection system can be held for consideration by a human inspector while other pellets proceed through the inspection phase wherein the pellet is supported by staging mechanism 66.

Pellets which have been inspected are preferably dropped into an inventory position wherein they are held by lower singular feed 123. The preferred manner of operation suggests that a determination be made as to the acceptability or nonacceptability of a particular fuel pellet before the pellet is discharged from the inventory above lower singular feed 123. Singular feed 123 can be manually or automatically controlled so that the appropriate routing is performed by routing means 130 as each individual pellet is individually discharged from singular feed 123. In this manner pellets are inspected and directed into either acceptable, unacceptable or other discharge fates.

Inspection systems constructed according to this invention can be manufactured of a variety of materials. Mechanical portions are preferably constructed of stainless steel when used in the nuclear industry for inspecting nuclear fuel pellets. In other applications a wide variety of either metallic or nonmetallic materials can be used as is well known in the art. Fiber optic light guides are constructed using present well known technology in the art. Lenses and other optical components can be made from glass or other suitable optical quality materials also well known in the art. The various components can be manufactured using well known machining and other manufacturing processes to produce the components shown and described herein or their equivalents.

The foregoing description of the preferred embodiments of the invention has been presented for purposes of illustration and description. It is not intended to be exhaustive or to limit the invention to the precise form disclosed, and obviously many modifications and variations are possible in light of the above teaching. The embodiments discussed in detail were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

I claim:

1. A remote inspection apparatus for optically inspecting exterior surfaces of objects, comprising:
    an enclosure;
    at least one inspection head mounted within the enclosure for receiving a supply of objects to be inspected; said inspection head having an object passageway extending downwardly thereinto, through which objects being inspected pass;
    collimating means for orienting the objects into a desired orientation for passage through the inspection head;
    transparent window means forming a section of said object passageway;
    a plurality of lens means arranged circumferentially about the window means for gathering and transmitting light reflected from surfaces of said objects;
    a plurality of light guide means receiving an optical image from said lens means and for conveying the optical images therethrough;
    a television camera for converting optical images conveyed by the light guide means into electronic signals representative of the optical images;
    signal processing means for integrating said electronic signals for producing a singular image of an object;
    a television monitor for converting said electronic signal into a visible image representative of surfaces of the objects;
    staging means for stationarily positioning an object within said window means so that exterior surfaces of the object can be viewed by the lens means;
    light source guides adjacent to the window means for beaming light onto objects positioned upon the staging means;
    first singular feed means for supplying objects to said staging means in a singular manner;
    second singular feed means below said staging means for holding inspected objects;
    at least two exit passageways through which objects can be directed depending upon the outcome of inspection; and
    controllable routing means for directing objects into one of said exit passageways.

* * * * *